United States Patent
Sato et al.

(10) Patent No.: US 6,822,112 B1
(45) Date of Patent: Nov. 23, 2004

(54) PROSTAGLANDIN DERIVATIVES

(75) Inventors: Fumie Sato, 2-1-901, Kugenumahigasi, Fujisawa-shi, Kanagawa 251-0026 (JP); Tohru Tanami, Tokyo (JP); Hideo Tanaka, Tokyo (JP); Naoya Ono, Tokyo (JP); Makoto Yagi, Tokyo (JP)

(73) Assignees: Taisho Pharmaceutical Co., Ltd. (JP); Fumie Sato (JP)

( * ) Notice: Subject to any disclaimer, the term of this patent is extended or adjusted under 35 U.S.C. 154(b) by 263 days.

(21) Appl. No.: 10/048,926
(22) PCT Filed: Aug. 11, 2000
(86) PCT No.: PCT/JP00/05422
 § 371 (c)(1),
 (2), (4) Date: Feb. 5, 2002
(87) PCT Pub. No.: WO01/12596
 PCT Pub. Date: Feb. 22, 2001

(30) Foreign Application Priority Data

Aug. 13, 1999 (JP) .............................. 11-229168

(51) Int. Cl.$^7$ ............................................. C07C 69/76
(52) U.S. Cl. .......................................... 560/63; 562/473
(58) Field of Search ............................ 560/64; 562/473

(56) References Cited

U.S. PATENT DOCUMENTS

| | | | |
|---|---|---|---|
| 4,029,681 A | 6/1977 | Smith | |
| 4,479,945 A | 10/1984 | Szekely et al. | |
| 4,638,002 A | 1/1987 | Szekely et al. | |
| 5,891,910 A | 4/1999 | Buchmann et al. | |
| 6,225,347 B1 | 5/2001 | Buchmann et al. | |

FOREIGN PATENT DOCUMENTS

| | | |
|---|---|---|
| JP | 52-100446 | 8/1977 |
| JP | 58-126835 | 7/1983 |
| JP | 2-502009 | 7/1990 |
| WO | 83/04021 | 5/1983 |

*Primary Examiner*—Paul J. Killos
(74) *Attorney, Agent, or Firm*—Lorusso, Loud & Kelly

(57) ABSTRACT

A prostaglandin derivative represented by the formula:

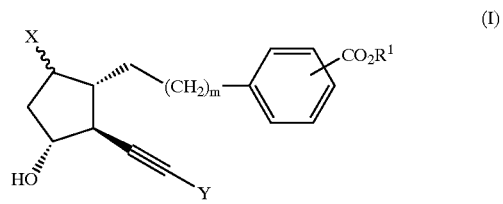

(I)

wherein X is a halogen atom, $R^1$ is a hydrogen atom, a $C_{1-10}$ alkyl group or a $C_{3-10}$ cycloalkyl group, m is an integer of 0 to 5, and Y is a group represented by the formula:

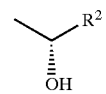

wherein $R^2$ is a $C_{3-10}$ cycloalkyl group, a $C_{3-10}$ cycloalkyl group substituted with $C_{1-4}$ alkyl group(s), a $C_{1-4}$ alkyl group substituted with $C_{3-10}$ cycloalkyl group(s), a $C_{1-10}$ alkyl group, a $C_{2-10}$ alkenyl group, a $C_{2-10}$ alkynyl group or a bridged cyclic hydrocarbon group, or a group represented by the formula:

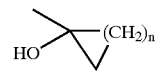

wherein n is an integer of 1 to 8; a pharmaceutically acceptable salt thereof or a hydrate thereof.

6 Claims, No Drawings

PROSTAGLANDIN DERIVATIVES

TECHNICAL FIELD

The present invention relates to novel prostaglandin derivatives, pharmaceutically acceptable salts thereof and hydrates thereof.

BACKGROUND ART

Since prostaglandin (hereinafter referred to as "PG") exhibits various important physiological actions in a trace amount, the syntheses of a great number of the derivatives from natural PGs and the biological activities have been investigated with the intention of a practical use as medicines and have been reported in Japanese Patent Kokai Sho 52-100446, Japanese Patent Kohyo Hei 2-502009, etc. Among them, Japanese Patent Kohyo Hei 2-502009 discloses a group of PG derivatives substituted with a halogen atom at the 9-position. In addition, PG derivatives having a $PGD_2$-like agonistic activity are reported by K-H Thierauch et al., in Drug of the Future, vol. 17, page 809 (1992).

DISCLOSURE OF THE INVENTION

As a result of the extensive studies, the present inventors have found that novel prostaglandin derivatives having a triple bond between the 13- and 14-positions represented by the following Formula (I) have an excellent $PGD_2$-like agonistic activity, and thereby the present invention has been accomplished.

That is, the present invention is directed to a prostaglandin derivative represented by Formula (I):

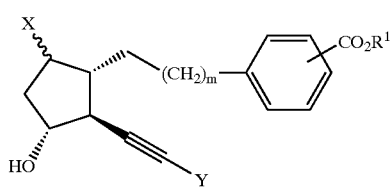

wherein X is a halogen atom, $R^1$ is a hydrogen atom, a $C_{1-10}$ alkyl group or a $C_{3-10}$ cycloalkyl group, m is an integer of 0 to 5, and Y is a group represented by the formula:

wherein $R^2$ is a $C_{3-10}$ cycloalkyl group, a $C_{3-10}$ cycloalkyl group substituted with $C_{1-4}$ alkyl group(s), a $C_{1-4}$ alkyl group substituted with $C_{3-10}$ cycloalkyl group(s), a $C_{1-10}$ alkyl group, a $C_{2-10}$ alkenyl group, a $C_{2-10}$ alkynyl group or a bridged cyclic hydrocarbon group, or a group represented by the formula:

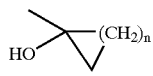

wherein n is an integer of 1 to 8; a pharmaceutically acceptable salt thereof or a hydrate thereof.

Furthermore, the present invention is directed to a pharmaceutical composition which comprises the compound represented by the general formula (I), the pharmaceutically acceptable salt thereof or the hydrate thereof.

MODE FOR CARRYING OUT THE INVENTION

In the present invention, the halogen atom refers to a fluorine atom, a chlorine atom, a bromine atom or an iodine atom.

Examples of the $C_{3-10}$ cycloalkyl group are a cyclopropyl group, a cyclobutyl group, a cyclopentyl group, a cyclohexyl group and a cycloheptyl group.

The $C_{1-10}$ alkyl group means a straight or branched alkyl group, and examples thereof are a methyl group, an ethyl group, a propyl group, an isopropyl group, a butyl group, an isobutyl group, a tert-butyl group, a pentyl group, an isopentyl group, a 2-ethylpropyl group, a hexyl group, an isohexyl group, a 1-ethylbutyl group, a heptyl group, an isoheptyl group, an octyl group, a nonyl group, a decyl group, a 1-methylpentyl group, a 2-methylpentyl group, a 1-methylhexyl group, a 2-methylhexyl group, a 2,4-dimethylpentyl group, a 2-ethylpentyl group, a 2-methylheptyl group, a 2-ethylhexyl group, a 2-propylpentyl group, a 2-propylhexyl group and a 2,6-dimethylheptyl group.

The $C_{2-10}$ alkenyl group means a straight or branched alkenyl group, and examples thereof are a vinyl group, an allyl group, a butenyl group, a 3-pentenyl group, a 4-hexenyl group, a 5-heptenyl group, a 4-methyl-3-pentenyl group, a 2,4-dimethyl-4-pentenyl group, a 6-methyl-5-heptenyl group and a 2,6-dimethyl-5-heptenyl group.

The $C_{2-10}$ alkynyl group means a straight or branched alkynyl group, and examples thereof are an ethynyl group, a 2-propynyl group, a 3-butynyl group, a 3-pentynyl group, a 3-hexynyl group, a 4-hexynyl group, a 1-methylpent-3-ynyl group, a 2-methylpent-3-ynyl group, a 1-methylhex-3-ynyl group and a 2-methylhex-3-ynyl group.

Examples of the bridged cyclic hydrocarbon group are a norbornyl group, an adamantyl group, a pinanyl group, a thujyl group, a caryl group, a bornyl group and a camphanyl group.

Examples of the pharmaceutically acceptable salt are salts with alkali metals (e.g., sodium or potassium), alkali earth metals (e.g., calcium or magnesium), ammonia, methylamine, dimethylamine, cyclopentylamine, benzylamine, piperidine, monoethanolamine, diethanolamine, monomethylmonoethanolamine, tromethamine, lysine, a tetraalkyl ammonium and tris (hydroxymethyl)aminomethane.

The compounds of Formula (I) can be prepared, for example, by the methods summarized by the following reaction scheme.

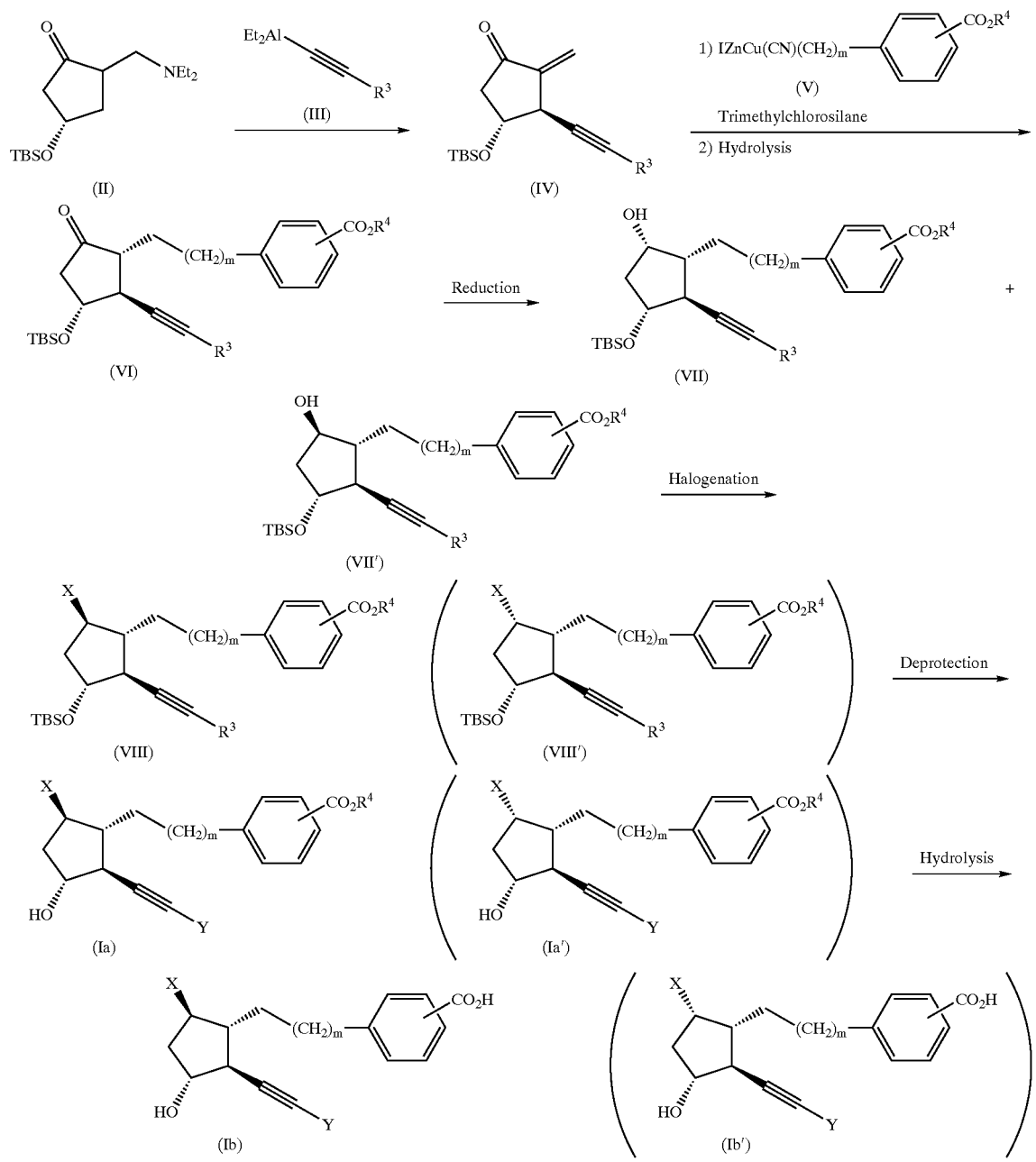

In the reaction scheme, TBS is a tert-butyldimethylsilyl group, $R^3$ is a group obtained by protecting the hydroxyl group in Y with TBS or a triethylsilyl group, $R^4$ is a straight or branched $C_{1-10}$ alkyl group or a $C_{3-10}$ cycloalkyl group, and X, Y and m are as defined above.

The above-mentioned reaction scheme is illustrated as follows:

(1) At first, a known compound of Formula (II) is reacted with 0.8 to 2.0 equivalents of an organic aluminum compound represented by Formula (III) in an inert solvent (e.g., benzene, toluene, tetrahydrofuran, diethyl ether, methylene chloride or n-hexane) at −10 to 30° C., preferably 0 to 10° C., according to the method of Sato et al. (*Journal of Organic Chemistry*, vol. 53, page 5590 (1988)) to stereospecifically give a compound of Formula (IV).

(2) The compound of Formula (IV) is reacted with 0.5 to 4.0 equivalents of an organic copper compound represented by Formula (V) and 0.5 to 4.0 equivalents of trimethylchlorosilane in an inert solvent (e.g., benzene, toluene, tetrahydrofuran, diethyl ether, methylene chloride, n-hexane or n-pentane) at −78 to 40° C., followed by hydrolysis using an inorganic acid (e.g., hydrochloric acid, sulfuric acid or nitric acid), an organic acid (e.g., acetic acid or p-toluenesulfonic acid) or an amine salt thereof (e.g., pyridinium p-toluenesulfonate) in an organic solvent (e.g., acetone, methanol, ethanol, isopropanol, diethyl ether or a mixture thereof) at 0 to 40° C. to stereoselectively give a compound of Formula (VI).

(3) The compound of Formula (VI) is reduced with 0.5 to 5 equivalents of a reductant (e.g., potassium borohydride, sodium borohydride, sodium cyanoborohydride, lithium trisec-butyl borohydride or 2,6-di-tert-butyl-p-cresol/ diisobutylaluminum hydride) in an organic solvent (e.g., tetrahydrofuran, diethyl ether, ethyl alcohol or methyl alcohol) at −78 to 40° C. to give compounds of Formulae (VII) and (VII'). These compounds of Formulae (VII) and (VII') can be purified by a conventional separation method such as column chromatography.

(4) The compound of Formula (VII) or (VII') is mesylated or tosylated, for example, with 1 to 6 equivalents of methanesulfonyl chloride or p-toluenesulfonyl chloride in a proper solvent such as pyridine (if necessary, in the presence of 0.8 to 6 equivalents of 4-dimethylaminopyridine) at −20 to 40° C., followed by chlorination with 1 to 16 equivalents of tetra-n-butylammonium chloride to give a compound of Formula (VIII) or (VIII') wherein X is a chlorine atom, respectively. Herein, bromination or fluorination can be also carried out in an ordinary manner. For example, bromination can be carried out by a reaction with 1 to 10 equivalents of carbon tetrabromide in the presence of 1 to 10 equivalents of triphenylphosphine and 1 to 10 equivalents of pyridine in acetonitrile. Fluorination can be carried out, for example, by a reaction with 5 to 20 equivalents of diethylaminosulfur trifluoride (DAST) in methylene chloride.

(5) The protective group (i.e., a tert-butyldimethylsilyl group or a triethylsilyl group) of the hydroxyl group of the compound of Formula (VIII) or (VIII') is removed by using hydrofluoric acid, pyridinium poly(hydrogenfluoride) or hydrochloric acid under conventional conditions in a solvent (e.g., methanol, ethanol, acetonitrile, a mixture thereof or a mixture of these solvents and water) to give a PG derivative of Formula (Ia) or (Ia') which is a compound of Formula (I) wherein $R^1$ is other than a hydrogen atom.

(6) The compound of Formula (Ia) or (Ia') is hydrolyzed using 1 to 6 equivalents of a base in a conventional solvent for hydrolysis to give a PG derivative of Formula (Ib) or (Ib') which is a compound of Formula (I) wherein $R^1$ is a hydrogen atom. Examples of the base are lithium hydroxide and potassium carbonate, and examples of the solvent are acetonitrile, acetone, methanol, ethanol, water and a mixture thereof.

The compounds of the present invention can be administered systemically or topically, or orally or parenterally in conventional dosage forms. For example, they can be administered orally in the form such as tablets, powders, granules, dusting powders, capsules, solutions, emulsions or suspensions, each of which can be prepared according to conventional methods. As the dosage forms for intravenous administration, there are used aqueous or non-aqueous solutions, emulsions, suspensions or solid preparations to be dissolved in a solvent for injection immediately before use. Furthermore, the compounds of the present invention can be formulated into the form of inclusion compounds with α-, β- or γ-cyclodextrin, or methylated cyclodextrin. In addition, the compounds of the present invention can be administered by injection in the form of aqueous or non-aqueous solutions, emulsions, suspensions, etc. The dose is varied by the age, body weight, etc., but it generally is from 1 ng to 1 mg/day per adult, which can be administered in a single dose or divided doses.

Representative compounds of Formula (I) of the present invention are shown in Tables 1 and 2.

TABLE 1

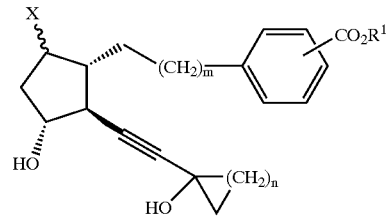

| | X | m | n | $CO_2R^1$ |
|---|---|---|---|---|
| Compound 1 | β-Cl | 1 | 3 | p-$CO_2Me$ |
| Compound 2 | β-Cl | 1 | 4 | p-$CO_2Me$ |
| Compound 3 | α-Cl | 1 | 4 | p-$CO_2Me$ |
| Compound 4 | β-Cl | 2 | 1 | p-$CO_2Me$ |
| Compound 5 | β-Cl | 2 | 2 | p-$CO_2Me$ |
| Compound 6 | β-Cl | 2 | 3 | o-$CO_2Me$ |
| Compound 7 | β-Cl | 2 | 3 | p-$CO_2tBu$ |
| Compound 8 | β-Cl | 2 | 3 | p-$CO_2Me$ |
| Compound 9 | β-Cl | 2 | 3 | p-$CO_2H$ |
| Compound 10 | α-Cl | 2 | 3 | p-$CO_2Me$ |
| Compound 11 | α-Cl | 2 | 3 | p-$CO_2H$ |
| Compound 12 | β-Cl | 2 | 4 | p-$CO_2Me$ |
| Compound 13 | β-Cl | 2 | 4 | p-$CO_2H$ |
| Compound 14 | α-Cl | 2 | 4 | p-$CO_2Me$ |
| Compound 15 | α-Cl | 2 | 4 | p-$CO_2H$ |
| Compound 16 | β-Br | 2 | 4 | p-$CO_2Me$ |
| Compound 17 | β-Br | 2 | 4 | p-$CO_2H$ |
| Compound 18 | F | 2 | 4 | p-$CO_2Me$ |
| Compound 19 | F | 2 | 4 | p-$CO_2H$ |
| Compound 20 | β-Cl | 3 | 4 | p-$CO_2Me$ |
| Compound 21 | β-Cl | 3 | 4 | p-$CO_2H$ |
| Compound 22 | β-Cl | 4 | 4 | p-$CO_2Me$ |
| Compound 23 | β-Cl | 4 | 4 | p-$CO_2H$ |
| Compound 24 | β-Cl | 5 | 4 | p-$CO_2Me$ |
| Compound 25 | β-Cl | 5 | 4 | p-$CO_2H$ |
| Compound 26 | β-Cl | 2 | 4 | m-$CO_2Me$ |
| Compound 27 | β-Cl | 2 | 5 | p-$CO_2Me$ |
| Compound 28 | β-Cl | 2 | 5 | p-$CO_2H$ |
| Compound 29 | β-Cl | 2 | 6 | p-$CO_2Me$ |

TABLE 2

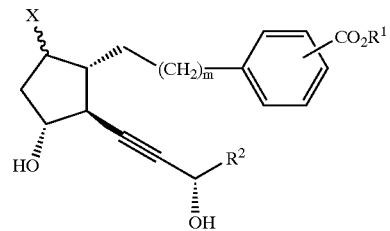

| | X | $R^2$ | m | $CO_2R^1$ |
|---|---|---|---|---|
| Compound 30 | β-Cl | cyclopentyl | 1 | p-$CO_2Me$ |
| Compound 31 | β-Cl | cyclopentyl | 2 | p-$CO_2Me$ |
| Compound 32 | β-Cl | cyclopentyl | 2 | p-$CO_2H$ |
| Compound 33 | β-Cl | cyclopentyl | 3 | p-$CO_2Me$ |
| Compound 34 | β-Cl | cyclohexyl | 2 | p-$CO_2Me$ |
| Compound 35 | β-Cl | cyclohexyl | 2 | p-$CO_2H$ |
| Compound 36 | α-Cl | cyclohexyl | 2 | p-$CO_2Me$ |
| Compound 37 | α-Cl | cyclohexyl | 2 | p-$CO_2H$ |
| Compound 38 | β-Cl | cyclohexyl | 2 | o-$CO_2Me$ |
| Compound 39 | β-Cl | cyclohexyl | 2 | o-$CO_2H$ |
| Compound 40 | β-Br | cyclohexyl | 2 | p-$CO_2Me$ |
| Compound 41 | β-Br | cyclohexyl | 2 | p-$CO_2H$ |
| Compound 42 | F | cyclohexyl | 2 | p-$CO_2Me$ |
| Compound 43 | F | cyclohexyl | 2 | p-$CO_2H$ |
| Compound 44 | β-Cl | cyclohexyl | 3 | p-$CO_2Me$ |
| Compound 45 | β-Cl | cycloheptyl | 2 | p-$CO_2Me$ |
| Compound 46 | β-Cl | cycloheptyl | 2 | p-$CO_2H$ |

TABLE 2-continued

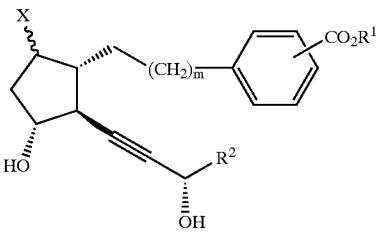

| | X | R² | m | CO₂R¹ |
|---|---|---|---|---|
| Compound 47 | β-Cl | cyclopentylmethyl | 2 | p-CO₂Me |
| Compound 48 | β-Cl | cyclopentylmethyl | 2 | p-CO₂H |
| Compound 49 | β-Cl | cyclohexylmethyl | 2 | p-CO₂Me |
| Compound 50 | β-Cl | cyclohexylmethyl | 2 | p-CO₂H |
| Compound 51 | β-Cl | (S)-2-methylhexyl | 2 | p-CO₂Me |
| Compound 52 | β-Cl | (S)-2-methylhexyl | 2 | p-CO₂H |
| Compound 53 | β-Cl | (R)-2-methylhexyl | 2 | p-CO₂Me |
| Compound 54 | β-Cl | (R)-2-methylhexyl | 2 | p-CO₂H |
| Compound 55 | β-Cl | (S)-2,6-dimethyl-5-heptenyl | 2 | p-CO₂Me |
| Compound 56 | β-Cl | (S)-2,6-dimethyl-5-heptenyl | 2 | p-CO₂H |
| Compound 57 | β-Cl | (R)-2,6-dimethyl-5-heptenyl | 2 | p-CO₂Me |
| Compound 58 | β-Cl | (R)-2,6-dimethyl-5-heptenyl | 2 | p-CO₂H |
| Compound 59 | β-Cl | (S)-1-methyl-3-hexynyl | 2 | p-CO₂Me |
| Compound 60 | β-Cl | (S)-1-methyl-3-hexynyl | 2 | p-CO₂H |
| Compound 61 | β-Cl | (R)-1-methyl-3-hexynyl | 2 | p-CO₂Me |
| Compound 62 | β-Cl | (R)-1-methyl-3-hexynyl | 2 | p-CO₂H | o: ortho substitution,
m: meta substitution,
p: para substitution

INDUSTRIAL APPLICABILITY

The compounds of the present invention have an excellent $PGD_2$-like agonistic activity, therefore they are useful as therapeutic agents of circulatory diseases such as renal diseases, ischemic heart diseases, heart failure or hypertension, and sleep-inducing agents.

The effect of the present invention is more specifically illustrated in the following experiment.

EXPERIMENT

Measurement of cAMP production promoting action in EBTr [NBL-4] cell derived from bovine embryonic trachea According to the method of Ito et al. in *Br. J. Pharmacol.*, vol. 99, page 13 (1990), the following test was carried out.

That is, EBTr [NBL-4] cells derived from bovine embryonic trachea (produced by Dainippon Pharmaceutical Co.) were inoculated on 24-well plates ($6 \times 10^4$ cells/well) (manufactured by Sumitomo Bakelite Co.), and cultured on a growth medium (MEM Earle's medium including 10% calf serum, 2 mM glutamine and non-essential amino acids) for 48 hours, followed by cultivation on 0.5 ml of a growth medium including the test compound and 0.5 mM 3-isobutyl-1-methylxanthine for 15 minutes. After the completion of the reaction, the cells were washed with a phosphate buffer (not including $Ca^{++}$ and $Mg^{++}$), 0.6 ml of 65% aqueous ethanol solution was added, followed by allowing to stand at 4° C. for an hour, and the resulting cAMP was extracted. After evaporation of the solvent by a centrifugal evaporator, the amount of cAMP was measured by using a cAMP EIA System (manufactured by Amersham Co.).

Results are shown in Table 3.

TABLE 3

| $1 \times 10^{-9}$ M (concentration of compound added) | cAMP production promoting action (percent to $PGD_2$) |
|---|---|
| Compound 35 | 150 |

It is found from the above results that Compound 35 has a cAMP production promoting action.

BEST MODE FOR CARRYING OUT THE INVENTION

The present invention is illustrated more specifically by the following examples. In the nomenclature of the compound such as, for example, 2,3,4-trinor-1,5-inter-m-phenylene, "nor" means the lack of a carbon chain at the position of interest, (i.e., in the above case, it means the lack of carbon chains at the. 2- to 4-positions), and "interphenylene" means the insertion of a benzene ring between carbon atoms (i.e., in the above case, it-means that each of the carbon atoms at the 1- and 5-positions binds to the benzene ring at the meta-position).

REFERENCE EXAMPLE 1

1-Ethynyl-1-triethylsiloxycyclopentane

To a dimethylformamide solution (49.5 ml) of 1-ethynyl-1-hydroxycyclopentane (5.45 g, 49.5 mmol) were added imidazole (6.74 g, 99.0 mmol) and triethylchlorosilane (9.97 ml, 59.4 mmol) at room temperature, followed by stirring for 30 minutes. The reaction solution was added to a mixture of n-hexane and a saturated aqueous sodium bicarbonate solution, and the organic layer was separated. The aqueous layer was extracted with hexane, and the organic layers were combined, washed with a saturated aqueous sodium bicarbonate solution and dried over anhydrous magnesium sulfate. After filtration, the filtrate was evaporated under reduced pressure to give the title compound (9.26 g).

b.p. 98° C./10.0 torr. $^1$H-NMR($CDCl_3$, 200 MHz) δ ppm; 0.45–1.15 (m, 15H), 1.48–2.04 (m, 8H), 2.43 (s, 1H); IR(neat); 3308, 2956, 2913, 2876, 1459, 1415, 1321, 1239, 1204, 1116, 1059, 1008, 946, 850, 743, 729, 655, 623, 519 $cm^{-1}$.

REFERENCE EXAMPLE 2

1-Ethynyl-1-triethylsiloxycyclohexane

Following the same manner as in Reference Example 1 using 1-ethynyl-1-hydroxycyclohexane in place of 1-ethynyl-1-hydroxycyclopentane in Reference Example 1, thereby the title compound was obtained.

b.p. 72° C./0.80 torr. $^1$H-NMR($CDCl_3$, 200 MHz) δ ppm; 0.58–0.78 (m, 6H), 0.87–1.08 (m, 9H), 1.14–1.95 (m, 10H), 2.45 (s, 1H); IR(neat); 3309, 2937, 2876, 1459, 1415, 1378, 1341, 1283, 1240, 1150, 1155, 1105, 1058, 1004, 950, 905, 884, 868, 843, 815, 797, 743, 728, 654, 626, 551, 519 $cm^{-1}$.

REFERENCE EXAMPLE 3

1-Ethynyl-1-triethylsiloxycycloheptane

Following the same manner as in Reference Example 1 using 1-ethynyl-1-hydroxycycloheptane in place of 1-ethynyl-1-hydroxycyclopentane in Reference Example 1, thereby the title compound was obtained.

b.p. 82° C./0.67 torr. $^1$H-NMR(CDCl$_3$, 200 MHz) δ ppm; 0.43–0.76 (m, 6H), 0.86–1.04 (m, 9H), 1.36–2.03 (m, 12H), 2.43 (s, 1H); IR(neat); 3308, 2935, 2876, 1459, 1415, 1378, 1282, 1239, 1190, 1070, 1006, 835, 743, 690, 654, 625, 544 cm$^{-1}$.

EXAMPLE 1

9-Deoxy-9β-chloro-2,3,4,16,17,18,19,20-octanor-1, 5-inter-p-phenylene-15,15-pentamethylene-13,14-didehydro-PGF$_1$α Methyl Ester (Compound 12)

(1) In toluene (72 ml) was dissolved 1-ethynyl-1-triethylsiloxycyclohexane (5.58 g, 23.4 mmol), and n-butyl lithium (2.5 M, hexane solution, 8.6 ml) was added at 0° C., followed by stirring at the same temperature for 30 minutes. To the solution was added diethylaluminum chloride (0.95 M, hexane solution, 26.5 ml) at 0° C., followed by stirring at room temperature for 30 minutes. To the solution was added (4R)-2-(N,N-diethylamino)methyl-4-(tert-butyldimethylsiloxy)cyclopent-2-en-1-one (0.25 M, toluene solution, 72 ml) at room temperature, followed by stirring for 15 minutes. The reaction solution, while stirring, was poured into a mixture of hexane (120 ml), a saturated aqueous ammonium chloride solution (170 ml) and an aqueous hydrochloric acid solution (3 M, 50 ml), and the organic layer was separated and washed with a saturated aqueous sodium bicarbonate solution (50 ml). The resulting organic layer was dried over anhydrous magnesium sulfate, filtered and concentrated, and the resulting residue was purified by a silica gel column chromatography (developing solvent; hexane:ethyl acetate=49:1) to give (3R,4R)-2-methylene-3-[3,3-pentamethylene-3-(triethylsiloxy)prop-1-ynyl]-4-(tert-butyldimethylsiloxy)cyclopentan-1-one (3.07 g).

$^1$H-NMR(CDCl$_3$, 200 MHz) δ ppm; 0.11 (s, 3H), 0.14 (s, 3H), 0.54–0.73 (m, 6H), 0.80–1.02 (m, 9H), 0.90 (s, 9H), 0.80–1.02 (m, 9H), 1.12–1.90 (m, 10H), 2.34 (dd, J=18.0, 7.1 Hz, 1H), 2.74 (dd, J=18.0, 6.4 Hz, 1H), 3.50–3.62 (m, 1H), 4.23–4.37 (m, 1H), 5.57 (dd, J=2.6, 0.7 Hz, 1H), 6.17 (dd, J=2.9, 0.7 Hz, 1H); IR(neat); 2935, 2876, 2858, 2209, 1736, 1715, 1621, 1462, 1412, 1362, 1289, 1255, 1104, 1063, 1005, 942, 905, 867, 837, 812, 779, 744, 672 cm$^{-1}$.

(2) Under an argon stream, copper (I) cyanide-dilithium dichloride (1.0 M, tetrahydrofuran solution, 2.9 ml) was added to 2-(4-carbomethoxyphenyl)ethyl zinc (II) iodide (0.88 M, tetrahydrofuran solution, 3.8 ml) at −70° C., followed by stirring at the same temperature for 20 minutes. To the solution were added the compound obtained in the above (1) (0.25 M, diethyl ether solution, 8.8 ml) and chlorotrimethylsilane (0.59 ml) at −70° C., and the temperature was raised to 0C with stirring over about an hour. The reaction solution, after addition of a saturated aqueous ammonium chloride solution, was extracted with hexane. The organic layer was washed with a saturated aqueous sodium bicarbonate solution and a saturated aqueous sodium chloride solution, dried over anhydrous magnesium sulfate, filtered and concentrated. The resulting residue was dissolved in diethyl ether (2.2 ml)—isopropyl alcohol (8.8 ml), and pyridinium p-toluenesulfonate (27.6 mg) was added, followed by stirring at room temperature for 12 hours. The reaction solution, after addition of hexane, was washed with a saturated aqueous sodium bicarbonate solution and a saturated aqueous sodium chloride solution, dried over anhydrous magnesium sulfate, filtered and concentrated, and the resulting residue was purified by a silica gel column chromatography (developing solvent; hexane:ethylacetate= 15:1) to give 2,3,4,16,17,18,19,20-octanor-1,5-inter-p-phenylene-15,15-pentamethylene-13,14-didehydro-PGE$_1$ methyl ester 11-(tert-butyldimethylsilyl)-15-triethylsilyl ether (730 mg).

$^1$H-NMR(CDCl$_3$, 200 MHz) δ ppm; 0.08 (s, 3H), 0.11 (s, 3H), 0.53–0.74 (m, 6H), 0.78–1.04 (m, 9H), 0.88 (s, 9H), 1.15–1.94 (m, 14H), 2.07–2.30 (m, 1H), 2.17 (dd, J=18.2, 6.8 Hz, 1H), 2.58–2.78 (m, 4H), 3.90 (s, 3H), 4.22–4.36 (m, 1H), 7.19–7.29 (m, 2H), 7.90–8.00 (m, 2H); IR(neat); 2934, 2875, 2858, 2232, 1929, 1747, 1725, 1611, 1461, 1436, 1414, 137.6., 1309, 1279, 1254, 1179, 1108, 1058, 1019, 1005, 971, 905, 8 68, 838, 811, 779, 744, 705, 671 cm$^{-1}$.

(3) A methyl alcohol solution (12 ml) of the compound obtained in (2) (730 mg) was cooled to 0° C., and potassium borohydride (126 mg) was added, followed by stirring for 15 minutes. After addition of water, extraction was carried out with ether, and the extract was washed with a saturated aqueous ammonium chloride solution and an aqueous sodium chloride solution, dried over anhydrous magnesium sulfate and filtered. The filtrate was concentrated under reduced pressure, and the resulting residue was purified by a silica gel column chromatography (developing solvent; n-hexane:AcOEt=10:1 to 3:2) to give 2,3,4,16,17,18,19,20-octanor-1,5-inter-p-phenylene-15,15-pentamethylene-13, 14-didehydro-PGF$_1$α methyl ester 11-(tert-butyldimethylsilyl)-15-triethylsilyl ether (279 mg) and 2,3, 4,16,17,18,19,20-octanor-1,5-inter-p-phenylene-15,15-pentamethylene-13,14-didehydro-PGF$_1$β methyl ester 11-(tert-butyldimethylsilyl)-15-triethylsilyl ether (401 mg).

2,3,4,16,17,18,19,20-Octanor-1,5-inter-p-phenylene-15,15-pentamethylene-13, 14-didehydro-PGF$_1$α Methyl Ester 11-(tert-Butyldimethylsilyl)-15-triethylsilyl Ether $^1$H-NMR(CDCl$_3$, 200 MHz) δ ppm; 0.09 (s, 3H), 0.10 (s, 3H), 0.55–0.72 (m, 6H), 0.83–1.02 (m, 9H), 0.88 (s, 9H), 1.13–2.07 (m, 17H), 2.42–2.52 (m, 1H), 2.57 (d, J=9.7 Hz, 1H), 2.66–2.78 (m, 2H), 3.90 (s, 3H), 4.05–4.20 (m, 1H), 4.23–4.34 (m, 1H), 7.23–7.30 (m, 2H), 7.91–7.99 (m, 2H); IR(neat); 3467, 2933, 2875, 2857, 2230, 1725, 1610, 1461, 1436, 1414, 1279, 1254, 1179, 1107, 1057, 1019, 1004, 868, 837, 778, 743, 705 cm$^{-1}$.

2,3,4,16,17,18,19,20-Octanor-1,5-inter-p-phenylene-15,15-pentamethylene-13,14-didehydro-PGF$_1$β Methyl Ester 11-(tert-Butyldimethylsilyl)-15-triethylsilyl Ether $^1$H-NMR(CDCl$_3$, 200 MHz) δ ppm; 0.07 (s, 3H), 0.08 (s, 3H), 0.55–0.73 (m, 6H), 0.82–1.04 (m, 9H), 0.87 (s, 9H), 1.17–1.94 (m, 18H), 2.25 (dd, J=9.2, 6.2 Hz, 1H), 2.70 (t, J=7.5 Hz, 1H), 3.86–4.29 (m, 2H), 3.90 (s, 3H), 7.21–7.29 (m, 2H), 7.90–8.01 (m, 2H); IR(neat); 3467, 2933, 2874, 2857, 2229, 1725, 1610, 1461, 1436, 1414, 1385, 1279, 1254, 1178, 1107, 1057, 1019, 1004, 868, 837, 778, 743, 705, 410 cm$^{-1}$.

(4) Under an argon stream, methanesulfonyl chloride (0.064 ml) was added to a pyridine solution (2.1 ml) of 2,3,4,16,17,18,19,20-octanor-1,5-inter-p-phenylene-15,15-pentamethylene-13,14-didehydro-PGF$_1$α methyl ester 11-(tert-butyldimethylsilyl)-15-triethylsilyl ether obtained in (3) (260 mg) at 0° C., followed by stirring at room temperature for 2 hours. To the solution was added a toluene solution (2.1 ml) of tetra-n-butylammonium chloride (1.84 g), followed by stirring at 45° C. overnight. To this was added water and, after extraction with n-hexane, the extract was washed with a saturated aqueous sodium chloride solution, dried over anhydrous magnesium sulfate and filtered. The filtrate was concentrated to give 9-deoxy-9β-chloro-2,3,4,16,17,18,19,20-octanor-1,5-inter-p-phenylene-15,15-pentamethylene-13,14-didehydro-PGF$_1$α methyl ester 11-(tert-butyldimethylsilyl)-15-triethylsilyl ether (232 mg) as a crude product.

Subsequently, this was dissolved in methanol (8.2 ml), and conc. hydrochloric acid (0.041 ml) was added at room temperature, followed by stirring for 2 hours. The reaction solution was added to a mixture of ethyl acetate and a saturated aqueous sodium bicarbonate solution, and the organic layer was separated. The aqueous layer was extracted with ethyl acetate, the organic layers were combined, washed with a saturated aqueous sodium bicarbonate solution, dried over anhydrous magnesium sulfate and filtered. The filtrate was concentrated under reduced pressure, and the resulting residue was purified by a silica gel column chromatography (developing solvent; n-hexane:AcOEt=3:1 to 2:1) to give the title compound (132 mg).

$^1$H-NMR(CDCl$_3$, 200 MHz) δ ppm; 1.12–2.37 (m, 20H), 2.72 (t, J=7.5 Hz, 2H), 3.86–4.02 (m, 1H), 3.91 (s, 3H), 4.36 (ddd, J=12.8, 6.4, 3.5 Hz, 1H), 7.22–7.30 (m, 2H), 7.91–8.00 (m, 2H); IR(neat); 3400, 2933, 2857, 2235, 1721, 1702, 1610, 1573, 1510, 1436, 1415, 1311, 1281, 1179, 1111, 1062, 1020, 963, 904, 852, 796, 763, 705, 530, 418 cm$^{-1}$.

EXAMPLE 2

9-Deoxy-9β-chloro-2,3,4,16,17,18,19,20-octanor-1,5-inter-p-phenylene-15,15-pentamethylene-13,14-didehydro-PGF$_1$α (Compound 13)

To a methanol (9.3 ml)—water (0.93 ml) solution of the compound obtained in Example 1 (117 mg) was added lithium hydroxide monohydrate (59 mg), followed by stirring at room temperature for 7 hours. The mixture was neutralized with 1N aqueous hydrochloric acid solution, followed by concentration. To the residue was added ethyl acetate (20 ml), the mixture was made acidic with 0.1N hydrochloric acid and salted out with ammonium sulfate, and the organic layer was separated. The organic layer was dried over anhydrous magnesium sulfate and filtered. The filtrate was concentrated under reduced pressure, and the resulting residue was purified by a silica gel column chromatography (developing solvent; n-hexane:AcOEt=1:1 to 1:2) to give the title compound (98.1 mg).

$^1$H-NMR(CDCl$_3$, 300 MHz) δ ppm; 1.10–1.98 (m, 17H), 2.10–2.34 (m, 3H), 2.30 (dd, J=9.7, 6.4 Hz, 1H), 2.74 (t, J=7.6 Hz, 2H), 3.89–4.00 (m, 1H), 4.31–4.40 (m, 1H), 7.25–7.33 (m, 2H), 7.98–8.05 (m, 2H); IR(neat); 3367, 2935, 2858, 2661, 2235, 1692, 1610, 1575, 1512, 1445, 1418, 1314, 1284, 1178, 1117, 1060, 1019, 961, 905, 852, 757, 703, 667, 637, 609, 530 cm$^{-1}$.

EXAMPLE 3

9-Deoxy-9β-chloro-2,3,4,16,17,18,19,20-octanor-1,5-inter-p-phenylene-15,15-tetramethylene-13,14-didehydro-PGF$_1$α Methyl Ester (Compound 8)

(1) Following the substantially same manner as in Example 1(1) using 1-ethynyl-1-triethylsiloxycyclopentane in place of 1-ethynyl-1-triethylsiloxycyclohexane in Example 1(1), thereby (3R,4R)-2-methylene-3-[3,3-tetramethylene-3-(triethylsiloxy)prop-1-ynyl]-4-(tert-butyldimethylsiloxy)cyclopentan-1-one was obtained.

H-NMR(CDCl$_3$, 200 MHz) δ ppm; 0.11 (s, 3H), 0.14 (s, 3H), 0.54–0.72 (m, 6H), 0.80–1.02 (m, 9H), 0.90 (s, 9H), 1.60–1.90 (m, 8H), 2.33 (dd, J=17.9, 7.4 Hz, 1H), 2.72 (dd, J=17.9, 6.5 Hz, 1H), 3.48–3.59 (m, 1H), 4.20–4.35 (m, 1H), 5.56 (dd, J=2.6, 0.7 Hz, 1H), 6.16 (dd, J=3.1, 0.7 Hz, 1H); IR(neat); 3401, 2955, 2876, 2210, 1737, 1714, 1621, 1463, 1412, 1362, 255, 1187, 1109, 1063, 1007, 941, 889, 837, 779, 744, 671cm$^{-1}$.

(2) Following the substantially same manner as in Example 1(2) using the compound obtained in the above (1), thereby2,3,4,16,17,18,19,20-octanor-1,5-inter-p-phenylene-15,15-tetramethylene-13,14-didehydro-PGE$_1$ methyl ester 11-tert-butyldimethylsilyl-15-triethylsilyl ether was obtained.

$^1$H-NMR(CDCl$_3$, 200 MHz) δ ppm; 0.08 (s, 3H), 0.11 (s, 3H), 0.54–0.72 (m, 6H), 0.79–1.02 (m, 9H), 0.88 (s, 9H), 1.20–1.90 (m, 12H), 2.16 (dd, J=18.3, 7.1 Hz, 1H), 2.15–2.30 (m, 1H), 2.60–2.75 (m, 4H), 3.90 (s, 3H), 4.20–4.34 (m, 1H), 7.19–7.29 (m, 2H), 7.90–8.00 (m, 2H); IR(neat); 2952, 2874, 2858, 1749, 1724, 1610, 1462, 1435, 1414, 1376, 1309, 1279, 1251, 1178, 1111, 1058, 1019, 971, 882, 837, 778, 764, 744, 705, 670, 418 cm$^{-1}$.

(3) Following the substantially same manner as in Example 1(3) using the compound obtained in the above (2), thereby 2,3,4,16,17,18,19,20-octanor-1,5-inter-p-phenylene-15,15-tetramethylene-13,14-didehydro-PGF$_1$α methyl ester 11-tert-butyldimethylsilyl-15-triethylsilyl ether and 2,3,4,16,17,18,19,20-octanor-1,5-inter-p-phenylene-15,15-tetramethylene-13,14-didehydro-PGF$_1$β methyl ester 11-tert-butyldimethylsilyl-15-triethylsilyl ether were obtained.

2,3,4,16,17,18,19,20-Octanor-1,5-inter-p-phenylene-15,15-tetramethylene-13,14-didehydro-PGF$_1$α Methyl Ester 11-tert-Butyldimethylsilyl-15-triethylsilyl Ether $^1$H-NMR(CDCl$_3$, 200 MHz) δ ppm; 0.09 (s, 3H), 0.10 (s, 3H), 0.54–0.70 (m, 6H), 0.88 (s, 9H), 0.84–1.00 (m, 9H), 1.50–2.06 (m, 15H), 2.39–2.56 (m, 1H), 2.50 (d, J=9.5 Hz, 1H), 2.64–2.80 (m, 2H), 3.90 (s, 3H), 4.06–4.18 (m, 1H), 4.24–4.30 (m, 1H), 7.20–7.32 (m, 2H), 7.88–8.00 (m, 2H); IR(neat); 3467, 2952, 2874, 2858, 2231, 1727, 1610, 1462, 1435, 1414, 1386, 1310, 1278, 1251, 1178, 1110, 1057, 1019, 970, 894, 837, 778, 744 cm$^{-1}$.

2,3,4,16,17,18,19,20-Octanor-1,5-inter-p-phenylene-15,15-tetramethylene-13,14-didehydro-PGF$_1$β Methyl Ester 11-tert-Butyldimethylsilyl-15-triethylsilyl Ether $^1$H-NMR(CDCl$_3$, 200 MHz) δ ppm; 0.07 (s, 3H), 0.08 (s, 3H), 0.55–0.73 (m, 6H), 0.88 (s, 9H), 0.85–1.02 (m, 9H), 1.44–2.00 (m, 16H), 2.22 (dd, J=9.3, 6.3 Hz, 1H), 2.71 (t, J=7.5 Hz, 2H), 3.90 (s, 3H), 3.88–4.04 (m, 1H), 4.16–4.30 (m, 1H), 7.20–7.32 (m, 2H), 7.90–8.02 (m, 2H); IR(neat); 3436, 2953, 2874, 2857, 2232, 1727, 1707, 1610, 1574, 1510, 1461, 1436, 1414, 1361, 1310, 1280, 1251, 1179, 1112, 1058, 1019, 971, 877, 836, 777, 765, 744, 706, 670 cm$^{-1}$.

(4) Following the substantially same manner as in Example 1(4) using 2,3,4,16,17,18,19,20-octanor-1,5-inter-p-phenylene-15,15-tetramethylene-13,14-didehydro-PGF$_1$α methyl ester 11-tert-butyldimethylsilyl-15-triethylsilyl ether obtained in the above (3), thereby the title compound was obtained.

$^1$H-NMR(CDCl$_3$, 300 MHz) δ ppm; 1.50–2.30 (m, 18H), 2.72 (t, J=7.7 Hz, 2H), 3.91 (s, 3H), 3.88–3.98 (m, 1H), 4.21–4.38 (m, 1H), 7.23–7.29 (m, 2H), 7.92–7.99 (m, 2H);

IR(neat); 3400, 2945, 2235, 1720, 1610, 1437, 1384, 1281, 1179, 1111, 1020, 763, 707, 499 cm$^{-1}$.

EXAMPLE 4

9-Deoxy-9β-chloro-2,3,4,16,17,18,19,20-octanor-1,5-inter-p-phenylene-15,15-tetramethylene-13,14-didehydro-PGF$_1$α (Compound 9)

Following the substantially same manner as in Example 2 using the compound obtained in Example 3, thereby the title compound was obtained.

$^1$H-NMR(CDCl$_3$, 300 MHz) δ ppm; 1.50–1.95 (m, 15H), 2.10–2.32 (m, 4H), 2.73 (t, J=7.5 Hz, 2H), 3.88–3.98 (m, 1H), 4.36–4.39 (m, 1H), 7.25–7.33 (m, 2H), 7.85–8.05 (m, 2H); IR(neat); 3367, 2942., 2861, 2657, 2235, 1691, 1610, 1575, 1512, 1419, 1315, 1284, 1178, 1087, 1019, 991, 946, 907, 857, 758, 703, 636, 524 cm$^{-1}$.

EXAMPLE 5

9-Deoxy-9β-chloro-2,3,4,16,17,18,19,20-octanor-1,5-inter-p-phenylene-15-cyclohexyl-13,14-didehydro-PGF$_1$α Methyl Ester (Compound 34)

(1) Following the substantially same manner as in Example 1(1) using (3S)-3-(tert-butyldimethylsiloxy)-3-cyclohexylprop-1-yne in place of 1-ethynyl-1-triethylsiloxycyclohexane in Example 1(1), thereby (3R,4R)-2-methylene-3-[(3S)-3-(tert-butyldimethylsiloxy)-3-cyclohexylprop-1-ynyl]-4-(tert-butyldimethylsiloxy)cyclopentan-1-one was obtained.

$^1$H-NMR(CDCl$_3$, 200 MHz) δ ppm; 0.08 (s, 3H), 0.10 (s, 6H), 0.13 (s, 3H), 0.83–1.92 (m, 11H), 0.90 (s, 18H), 2.33 (dd, J=17.9, 7.4 Hz, 1H), 2.72 (dd, J=17.9, 6.5 Hz, 1H), 3.49–3.58 (m, 1H), 4.13 (dd, J=6.1, 1.6 Hz, 1H), 4.22–4.34 (m, 1H), 5.56 (dd, J=2.7, 0.7 Hz, 1H), 6.14 (dd, J=3.1, 0.7 Hz, 1H); IR(neat):2929, 2856, 2234, 1737, 1645, 1473, 1463, 1451, 1381, 1362, 1245, 1104, 1006, 899, 838, 778, 669 cm$^{-1}$.

(2) Following the substantially same manner as in Example 1(2) using the compound obtained in the above (1), thereby 2,3,4,16,17,18,19,20-octanor-1,5-inter-p-phenylene-15-cyclohexyl-13, 14-didehydro-PGE$_1$ methyl ester 11,15-bis(tert-butyldimethylsilyl ether) was obtained.

$^1$H-NMR(CDCl$_3$, 200 MHz) δ ppm; 0.06 (s, 3H), 0.08 (s, 6H), 0.11 (s, 3H), 0.74–1.90 (m, 15H), 0.88 (s, 9H), 0.89 (s, 9H), 2.06–2.30 (m, 1H), 2.16 (dd, J=18.3, 7.1 Hz, 1H), 2.57–2.76 (m, 4H), 3.90 (s, 3H), 4.07 (dd, J=6.2, 1.5 Hz, 1H), 4.21–4.35 (m, 1H), 7.19–7.28 (m, 2H), 7.89–8.01 (m, 2H); IR(neat); 2929, 2855, 2234, 1746, 1723, 1610, 1471, 1462, 1436, 1413, 1361, 1279, 1252, 1179, 1109, 1020, 939, 897, 837, 778, 705, 670 cm$^{-1}$.

(3) Following the substantially same manner as in Example 1(3) using the compound obtained in the above (2), thereby 2,3,4,16,17,18,19,20-octanor-1,5-inter-p-phenylene-15-cyclohexyl-13,14-didehydro-PGF$_1$α methyl ester 11,15-bis(tert-butyldimethylsilyl ether) and 2,3,4,16,17,18,19,20-octanor-1,5-inter-p-phenylene-15-cyclohexyl-13,14-didehydro-PGF$_1$ methyl ester 11,15-bis(tert-butyldimethylsilyl ether) were obtained.

2,3,4,16,17,18,19,20-Octanor-1,5-inter-p-phenylene-15-cyclohexyl-13,14-didehydro-PGF$_1$α Methyl Ester 11,15-bis(tert-Butyldimethylsilyl Ether)

$^1$H-NMR(CDCl$_3$, 200 MHz) δ ppm; 0.06 (s, 3H), 0.07 (s, 3H), 0.09 (s, 3H), 0.10 (s, 3H), 0.88 (s, 9H), 0.89 (s, 9H), 0.95–2.06 (m, 18H), 2.39–2.50 (m, 1H), 2.55 (d, J=9.7 Hz, 1H), 2.64–2.76 (m, 2H), 3.90 (s, 3H), 4.02–4.18 (m, 1H), 4.05 (dd, J=6.4, 2.0 Hz, 1H), 4.24–4.32 (m, 1H), 7.21–7.31 (m, 2H), 7.87–8.00 (m, 2H); IR(neat); 3467, 2929, 2855, 2234, 1726, 1610, 1471, 1463, 1435, 1361, 1278, 1251, 1178, 1107, 1020, 898, 836, 777, 705, 668 cm-1.

2,3,4,16,17,18,19,20-Octanor-1,5-inter-p-phenylene-15-cyclohexyl-13,14-didehydro-PGF$_1$β Methyl Ester 11,15-bis(tert-Butyldimethylsilyl Ether)

$^1$H-NMR(CDCl$_3$, 200 MHz δ ppm; 0.06 (s, 6H), 0.07 (s, 3H), 0.09 (s, 3H), 0.83–1.92 (m, 19H), 0.87 (s, 9H), 0.89 (s, 9H), 2.23 (ddd, J=9.2, 6.2, 1.6 Hz, 1H), 2.70 (t, J=7.6 Hz, 2H), 3.90 (s, 3H), 3.86–4.03 (m, 1H), 4.06 (dd, J=6.3, 1.6 Hz, 1H), 4.15–4.29 (m, 1H), 7.20–7.30 (m, 2H), 7.90–8.00 (m, 2H); IR(neat); 3435, 2928, 2855, 2234, 1726, 1707, 1610, 1471, 1462, 1436, 1414, 1388, 1361, 1337, 1310, 1279, 1251, 1178, 1109, 1067, 1020, 1006, 962, 939, 927, 898, 836, 777, 705, 669 cm$^{31\ 1}$.

(4) Following the substantially same manner as in Example 1(4) using 2,3,4,16,17,18,19,20-octanor-1,5-inter-p-phenylene-15-cyclohexyl-13,14-didehydro-PGF$_1$α methyl ester 11,15-bis(tert-butyldimethylsilyl ether) obtained in the above (3), thereby 9-deoxy-9β-chloro-2,3,4,16,17,18,19,20-octanor-1,5-inter-p-phenylene-15-cyclohexyl-13,14-didehydro-PGF$_1$α methyl, ester 11,15-bis(tert-butyldimethylsilyl ether) was obtained.

$^1$H-NMR(CDCl$_3$, 200 MHz) δ ppm; 0.06 (s, 6H), 0.07 (s, 3H), 0.09 (s, 3H), 0.74–1.90 (m, 15H), 0.86 (s, 9H), 0.89 (s, 9H), 2.02–2.20 (m, 3H), 2.23–2.33 (m, 1H), 2.70 (t, J=7.0 Hz, 2H), 3.86–3.98 (m, 1H), 3.91 (s, 3H), 4.06 (dd, J=6.3, 1.4 Hz, 1H), 4.19–4.29 (m, 1H), 7.21–7.31 (m, 2H), 7.90–8.01 (m, 2H); IR(neat); 2929, 2855, 2235, 1726, 1610, 1471, 1462, 1435, 1413, 1385, 1361, 1278, 1252, 1178, 1106, 1071, 1021, 898, 836, 777, 704 cm$^{-1}$.

(5) Following the substantially same manner as in Example 1(5) using the compound obtained in the above (4), thereby the title compound was obtained.

$^1$H-NMR(CDCl$_3$, 200 MHz) δ ppm; 0.97–2.05 (m, 17H), 2.12–2.34 (m, 4H), 2.71 (t, J=7.70 Hz, 2H), 3.89–3.99 (m, 1H), 3.91 (s, 3H), 4.10–4.18 (m, 1H), 4.32–4.42 (m, 1H), 7.23–7.29 (m, 2H), 7.93–7.99 (m, 2H); IR(neat); 3400, 2928, 2853, 2235, 1721, 1610, 1574, 1510, 1436, 1415, 1311, 1281, 1179, 1110, 1020, 893, 857, 764, 705 cm$^{-1}$.

EXAMPLE 6

9-Deoxy-9β-chloro-2,3,4,16,17,18,19,20-octanor-1,5-inter-p-phenylene-15-cyclohexyl-13,14-didehydro-PGF$_1$α (Compound 35)

Following the substantially same manner as in Example 2 using the compound obtained in Example 5, thereby the title compound was obtained.

$^1$H-NMR(CDCl$_3$, 300 MHz) δ ppm; 0.90–1.95 (m, 18H), 2.10–2.35 (m, 4H), 2.73 (t, J=7.6 Hz, 2H), 3.88–4.00 (m, 1H), 4.13 (dd, J=6.0, 1.8 Hz, 1H), 4.31–4.41 (m, 1H), 7.24–7.33 (m, 2H), 7.97–8.07 (m, 2H); IR(neat); 3367, 2929, 2853, 2662, 2236, 1932, 1692, 1610, 1575, 1512, 1449, 1418, 1314, 1261, 1178, 1084, 1018, 948, 893, 858, 798, 757, 702, 667, 636, 545 cm$^{-1}$.

What is claimed is:

1. A prostaglandin derivative represented by Formula (I):

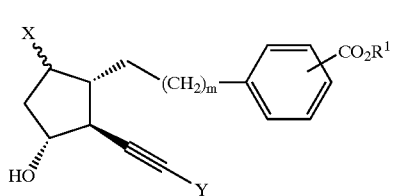
(I)

wherein X is a halogen atom, $R^1$ is a hydrogen atom, a $C_{1-10}$ alkyl group or a $C_{3-10}$ cycloalkyl group, m is an integer of 0 to 5, and Y is a group represented by the formula:

wherein $R^2$ is a $C_{3-10}$ cycloalkyl group, a $C_{3-10}$ cycloalkyl group substituted with $C_{14}$ alkyl group(s), a $C_{14}$ alkyl group substituted with $C_{3-10}$ cycloalkyl group(s), a $C_{1-10}$ alkyl group, a $C_{2-10}$ alkenyl group, a $C_{2-10}$ alkynyl group or a bridged cyclic hydrocarbon group, or a group represented by the formula:

wherein n is an integer of 1 to 8; a pharmaceutically acceptable salt thereof or a hydrate thereof.

2. The prostaglandin derivative of Formula (I) according to claim 1 wherein Y is a group represented by the formula:

wherein $R^2$ is a $C_{3-10}$ cycloalkyl group, a $C_{3-10}$ cycloalkyl group substituted with $C_{1-4}$ alkyl group(s), a $C_{1-4}$ alkyl group substituted with $C_{3-10}$ cycloalkyl group(s), a $C_{5-10}$ alkyl group, a $C_{5-10}$ alkenyl group, a $C_{5-10}$ alkynyl group or a bridged cyclic hydrocarbon group; the pharmaceutically acceptable salt thereof or the hydrate thereof.

3. The prostaglandin derivative of Formula (I) according to claim 1 wherein Y is a group represented by the formula:

wherein n is an integer of 1 to 8; the pharmaceutically acceptable salt thereof or the hydrate thereof.

4. The prostaglandin derivative of Formula (I) according to claim 1 wherein X is a chlorine atom or a bromine atom; the pharmaceutically acceptable salt thereof or the hydrate thereof.

5. The prostaglandin derivative of Formula (I) according to claim 1 wherein Y is a group of the formula:

wherein n is 3 to 5; the pharmaceutically acceptable salt thereof or the hydrate thereof.

6. A pharmaceutical composition which comprises the prostaglandin derivative according to claim 1; the pharmaceutically acceptable salt thereof or the hydrate thereof.

* * * * *

UNITED STATES PATENT AND TRADEMARK OFFICE
CERTIFICATE OF CORRECTION

PATENT NO.     : 6,822,112 B1
DATED          : November 23, 2004
INVENTOR(S)    : Fumie Sato et al.

It is certified that error appears in the above-identified patent and that said Letters Patent is hereby corrected as shown below:

Title page,
Item [30], Foreign Application Priority Data, change "11-229168" to
-- 229168/1999 --;

Column 8,
Line 10, add -- (Note) Compound 35 in Table 7 is one which was prepared in the example described below. The test compound was used as a form of an ethanol solution, and compared with a vehicle-treated group as a control. --;

Column 9,
Line 19, change "add6d" to -- added --;
Line 51, change "0C" to -- 0ºC --;

Column 10,
Line 10, change "137.6.," to -- 1376, --;

Column 11,
Line 66, change "H-NMR" to -- $^1$H-NMR --;

Column 12,
Line 5, change "255" to -- 1255 --;

Column 13,
Line 60, change "$PGF_1$" to -- $PGF_1\beta$ --;

UNITED STATES PATENT AND TRADEMARK OFFICE
CERTIFICATE OF CORRECTION

PATENT NO. : 6,822,112 B1
DATED : November 23, 2004
INVENTOR(S) : Fumie Sato et al.

It is certified that error appears in the above-identified patent and that said Letters Patent is hereby corrected as shown below:

Column 14,
Line 21, change "$cm^{31}$" to -- $cm^{-1}$ --;

Column 15,
Line 23, change "$C_{14}$" to -- $C_{1-4}$ --, both instances.

Signed and Sealed this

Eighth Day of November, 2005

JON W. DUDAS
*Director of the United States Patent and Trademark Office*